Figure 1:
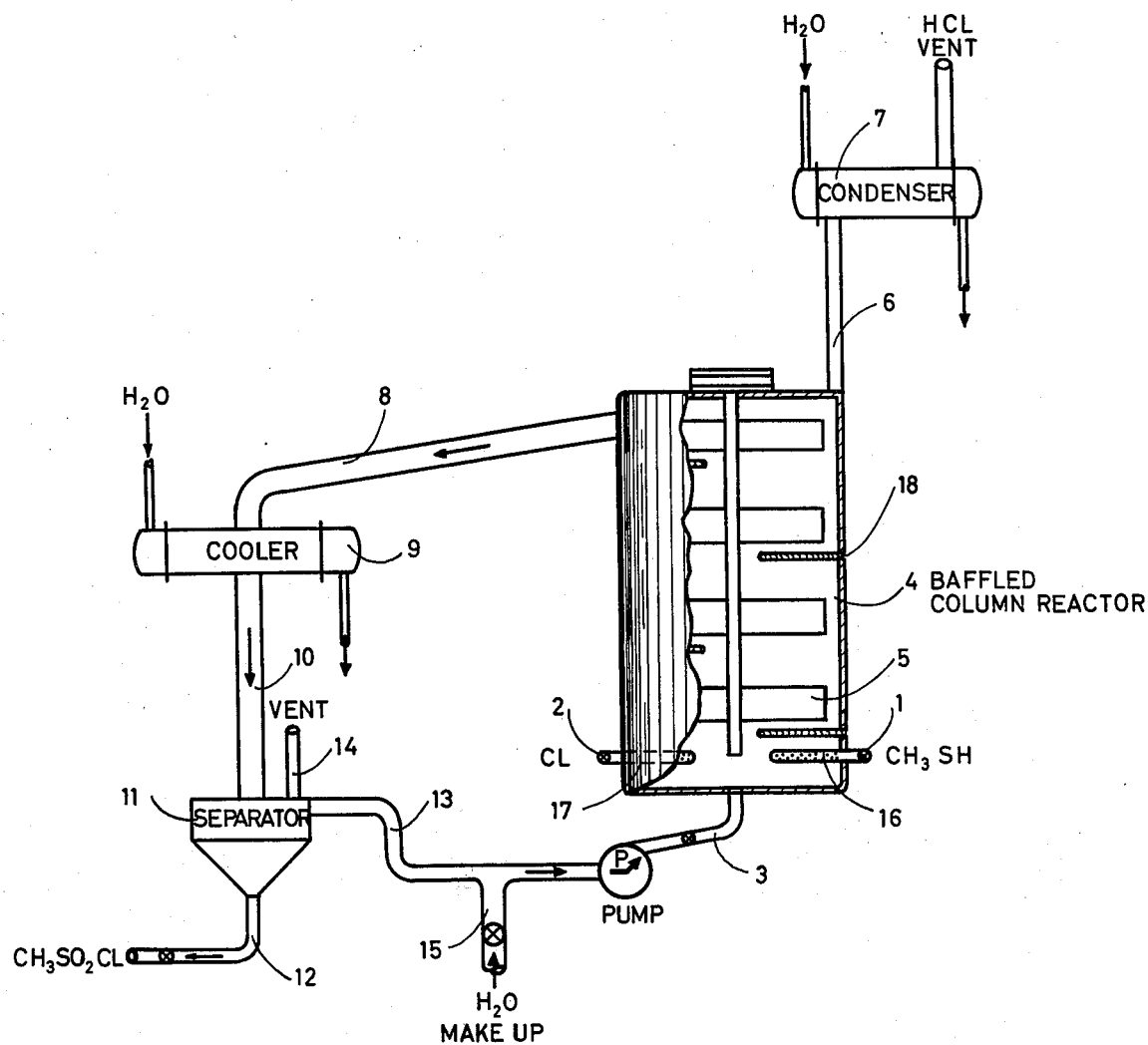

United States Patent [19]

Giolito et al.

[11] 3,993,692

[45] Nov. 23, 1976

[54] METHANE SULFONYL CHLORIDE AND PROCESS OF PREPARATION

[75] Inventors: Silvio L. Giolito, Whitestone; Harry O. Hofmann, Yonkers, both of N.Y.

[73] Assignee: Stauffer Chemical Company, Westport, Conn.

[22] Filed: Apr. 30, 1969

[21] Appl. No.: 824,358

Related U.S. Application Data

[63] Continuation of Ser. No. 518,199, Jan. 3, 1966, abandoned.

[52] U.S. Cl............................................. 260/543 R
[51] Int. Cl.$^2$...................................... C07C 143/70
[58] Field of Search ................................ 260/543 R

[56] References Cited
UNITED STATES PATENTS

| | | | |
|---|---|---|---|
| 2,772,307 | 11/1956 | Park | 260/543 R |
| 3,248,423 | 4/1966 | Stratton | 260/543 R |

FOREIGN PATENTS OR APPLICATIONS 801,037   9/1958   United Kingdom............. 260/593 R

OTHER PUBLICATIONS

Gilbert, Sulfonation and Related Reactions, pp. 202–208 (1965), Interscience Publishers, New York, N.Y.
Hougen et al., Chemical Process Principles, Part 1, Second Edition (1959).
Handbook of Chemistry & Physics, 50th Edition, p. C–70 (1969–1970).

*Primary Examiner*—D. Horwitz
*Attorney, Agent, or Firm*—Daniel S. Ortiz

[57] ABSTRACT

A continuous process for preparing methane sulfonyl chloride by the reaction of methyl mercaptan with chlorine in the presence of an aqueous bath of hydrogen chloride at an elevated temperature.

4 Claims, 1 Drawing Figure

U.S. Patent

Nov. 23, 1976

3,993,692

METHANE SULFONYL CHLORIDE AND PROCESS OF PREPARATION

This application is a continuation of application Ser. No. 518,199, filed Jan. 3, 1966, now abandoned.

This invention relates to a process for the production of methane sulfonyl chloride. More particularly, it relates to a continuous process for the preparation of methane sulfonyl chloride by the simultaneous hydrolysis and chlorination of methyl mercaptan.

Methane sulfonyl chloride (sometimes referred to as mesyl chloride) is an old compound having many known uses. For example, it is used as an intermediate in the manufacture of corticosteroids, dyestuffs and other organic chemicals. Several of its esters are also effective in treating leukemia and tumorous growths. Because of its many uses, several methods of preparing methane sulfonyl chloride and the other sulfonyl chlorides have been developed. For example, one method involves reacting dimethylsulfoxide and chlorine in an aqueous medium. The reaction between a higher alkyl mercaptan and chlorine in an aqueous medium was investigated in some early work by Douglass and Johnson, J. Am. Chem. Soc. Vol. 60, pages 1486–1489 (with ethyl and N-amyl mercaptan at temperatures from 0° to 10° C.). From this and other reported work (Reid "Organic Chemistry of Bivalent Sulfur", Vol. 1, pages 124–125) it has heretofore been thought that the reaction must be conducted at low temperatures in order to prevent the formation of methane sulfonic acid. In addition, the tendency for local hot spots to develop and cause the ignition of the methyl mercaptan also dictated low temperatures. These facts and others seemed to preclude the use of elevated temperatures, much less a continuous process.

It is an object of this invention to provide a continuous process for the preparation of methane sulfonyl chloride by the simultaneous hydrolysis and chlorination of methyl mercaptan at elevated temperatures.

Another object of the invention is to provide a continuous process for the preparation of methane sulfonyl chloride by the simultaneous hydrolysis and chlorination of methyl mercaptan at elevated temperatures, which process produces a pure product in high yields.

Other objects will be apparent from the description which follows.

We have now discovered that methane sulfonyl chloride may be prepared by the simultaneous hydrolysis and chlorination of methyl mercaptan using gaseous methyl mercaptan with gaseous chlorine at elevated temperatures in a saturated aqueous hydrochloric acid reaction matrix. The hydrogen chloride formed by reaction is in part entrained in the aqueous reaction matrix which, after cooling and separation from the methane sulfonyl chloride product, is recycled to the reactor. This aqueous hydrochloric acid acts partly as a diluent for the reactants but primarily it is instrumental in moderating the heat of reaction. The hydrogen chloride formed from the reaction is discarded or recovered by well-known means. Because water is consumed in the reaction, it is necessary to periodically add make-up water or concentrated aqueous hydrochloric acid, which addition may be done at any convenient point in the apparatus. The methane sulfonyl chloride product is continuously separated by cooling the reaction mixture and phase separating the relatively dense methane sulfonyl chloride product. To remove the very minor amount of water, hydrochloric acid, chlorine, and unreacted mercaptan which is admixed with the product, said product is dried under reduced pressure. The lighter aqueous hydrochloric acid phase may also contain a very minor amount of product, but this may be recovered by extraction with an inert organic solvent such as benzene.

By the process of this invention, one may conduct the reaction at a temperature between about 3° and 85° C., which is referred to in the specification and claims as "elevated temperatures." If the reaction is to be run at lower temperatures, considerable cooling is required and at higher temperatures the risk of ignition of the reactants is high; consequently, a preferred temperature range is from about 40° to about 75° C.

To provide a thorough mixing of the reactants, we have found that a vertical baffled column reactor fitted with a full length paddle agitator is preferred. The residence time of the reactants in the reactor should be at least 3 seconds and preferably from 3 to about 60 seconds. Means are provided at or near the base of the reactor column for metering separately gaseous streams of methyl mercaptan and chlorine as well as means for introducing the recycled aqueous hydrochloric acid. To prevent the formation of large bubbles and the consequent danger of ignition of the methyl mercaptan, the gaseous chlorine and mercaptan entrance conduits to the reactor may be fitted with gas spargers. Such spargers will help disperse the reactants quickly in the aqueous hydrochloric acid. It is also desirable to cool the outer surface of the column reactor and this may be done by either using a cooling jacket or by simply introducing a thin film of water at the top of the reactor and allowing said water to cascade down the sides. The reactor is preferably vented near the top through a knock-out condenser so that the excess hydrogen chloride formed from the reaction does not carry out entrained methane sulfonyl chloride product or water vapor. Although a packed column may also be used, an agitated column is preferred.

After reaction is complete, the methane sulfonyl chloride product in the saturated aqueous hydrochloric acid phase is passed out of the reactor into one or more coolers. In the cooler the temperature of the aqueous hydrochloric acid is lowered to about 50° C. and preferably about 40° C. The more dense methane sulfonyl chloride product is separated after cooling and may be stripped under reduced pressure to remove the volatiles to produce a product having a 99 + % purity.

Referring now to FIG. 1, the invention may be described in a preferred embodiment as follows:

Methyl mercaptan is passed through valved conduit 1 to gas sparger 16, chlorine through valved conduit 2 to gas sparger 17, and saturated aqueous hydrochloric acid through valved conduit 3 into a baffled column reactor 4 having a paddle agitator 5. A paddle is shown at 18. Hydrogen chloride formed from the reaction is passed via conduit 6 through condenser 7 to a vent. Any water vapor entrained in the hydrogen chloride is condensed in condenser 7 and returned through conduit 6 to baffled column reactor 4. The uprising reaction matrix is passed through conduit 8 into cooler 9; then through conduit 10 to separator 11 where the more dense methane sulfonyl chloride product is separated and passed through valved conduit 12 and the saturated aqueous hydrochloric acid is passed through conduit 13 to be returned to baffled column reactor 4.

Entrained gaseous HCl is vented from separator 11 through vent 14. Makeup water is introduced into the recycled saturated aqueous hydrochloric acid through valved conduit 15.

The following example which is illustrative of the invention should not be construed as limiting the invention in any way. All parts in the following example are by weight.

EXAMPLE 1

To a column reactor of the type previously described is charged 24 parts per hour of gaseous methyl mercaptan, 110 parts per hour of gaseous chlorine and an excess of saturated aqueous hydrochloric acid, said hydrochloric acid being at a temperature of 40° C. The temperature of the reaction mixture is maintained between about 50° and about 75° C. by allowing a thin stream of water to cascade down the outer shell of the reactor. The reaction mixture which is passed to a cooler is then phase separated to allow the methane sulfonyl chloride product to be collected at a rate of 52 parts per hour. After removing the volatiles by stripping under reduced pressure, the product is 99% pure methane sulfonyl chloride having a yield calculated as 92% of theoretical.

From the foregoing detailed description and example, it will be apparent to one skilled in the art that obvious variations and modifications can be made without departing from the true spirit and scope of the invention.

What is claimed is:

1. A continuous process for producing methane sulfonyl chloride comprising:
    a. maintaining a liquid bath consisting essentially of saturated aqueous hydrochloric acid with methane sulfonyl chloride dispersed therein at a temperature between about 40° C. and about 75° C.;
    b. continuously introducing gaseous methyl mercaptan, chlorine and a liquid consisting essentially of water or aqueous hydrogen chloride into said bath for reaction to produce methane sulfonyl chloride and hydrogen chloride;
    c. withdrawing gaseous material consisting essentially of hydrogen chloride formed by the reaction;
    d. withdrawing substantially continuously a portion of the liquid from said bath and isolating methane sulfonyl chloride therefrom.

2. The process of claim 1 wherein the hydrochloric acid withdrawn from the liquid bath and isolated from the organic material is returned to the liquid bath.

3. The process of claim 1 wherein the gaseous material withdrawn from the liquid bath is cooled to produce a cooled vapor phase and a liquid phase, and said liquid phase is returned to said liquid bath.

4. The process of claim 1 wherein the liquid bath is agitated to maintain said methane sulfonyl chloride dispersed in said hydrochloric acid.

* * * * *